United States Patent [19]
Reilly et al.

[11] Patent Number: 5,520,653
[45] Date of Patent: May 28, 1996

[54] SYRINGE ADAPTER FOR FRONT-LOADING MEDICAL INJECTOR

[75] Inventors: David M. Reilly, Glenshaw; Joseph B. Havrilla, Pittsburgh, both of Pa.

[73] Assignee: Medrad, Inc., Pittsburgh, Pa.

[21] Appl. No.: 522,777

[22] Filed: Sep. 1, 1995

[51] Int. Cl.⁶ ................................................ A61M 1/00
[52] U.S. Cl. .................... 604/152; 604/131; 128/DIG. 1
[58] Field of Search .................................. 604/151–155, 604/181, 187, 131, 134, 140, 143, 218, 228, 232; 128/655, DIG. 1

[56] References Cited

U.S. PATENT DOCUMENTS

| | | |
|---|---|---|
| 3,880,163 | 4/1975 | Ritterskamp . |
| 4,677,980 | 1/1987 | Reilly et al. . |
| 5,269,762 | 12/1993 | Armbruster et al. . |
| 5,279,569 | 1/1994 | Neer et al. . |
| 5,383,858 | 1/1995 | Reilly et al. . |

Primary Examiner—C. Fred Rosenbaum
Assistant Examiner—Perry E. Van Over
Attorney, Agent, or Firm—Gretchen Platt Stubenvoll

[57] ABSTRACT

The adapters of the present invention are used for releasably attaching syringes of various types having a body, a plunger reciprocally mounted therein, and a flange near the rear end of the syringe body, to a front-loading injector head. In a preferred embodiment, the adapter includes a syringe carrier having a front end, a rear end, and syringe retaining channel located between the carrier front and rear ends for engaging at least a portion of the syringe flange; mounting flanges near the carrier rear end for releasably mounting the carrier in a desired position relative to the front wall of the injector head; a follower reciprocally mounted within the carrier having a front end engagable with the syringe plunger when the syringe is installed in the carrier; and a drive head opening communicating with a pair of drive head slots positioned proximate to the rear end of the follower for releasably mounting the follower in a desired position relative to the drive head of the injector head.

20 Claims, 8 Drawing Sheets

SYRINGE ADAPTER FOR FRONT-LOADING MEDICAL INJECTOR

FIELD OF THE INVENTION

The present invention relates to adapters for releasably attaching syringes to medical injectors, and more particularly to adapters for releasably attaching syringes of various types to front-loading injectors.

BACKGROUND OF THE INVENTION

Medical injectors and syringes containing fluid, such as contrast media, are commonly used to inject fluid into a patient in a wide variety of diagnostic procedures. Injectors of the front-loading type are often used in such procedures. U.S. Pat. No. 5,383,858, assigned to the common assignee of the present application, provides a detailed description of injectors of the front-loading type and corresponding syringe designs, and is fully incorporated herein by reference. One advantage of the front-loading injector of U.S. Pat. No. 5,383,858 is that a syringe can readily be loaded onto and removed from the injector head without the need to disconnect the fluid path from the syringe to the patient. Another advantage of the front-loading injector of U.S. Pat. No. 5,383,858 is that the drive means of the injector head may be disengaged and retracted from the syringe plunger without retracting the syringe plunger, thus substantially reducing the risk of withdrawing fluid from the patient after completion of the diagnostic procedure. This feature is also taught in U.S. Pat. No. 4,677,980, assigned to the common assignee of the present application, and fully incorporated herein by reference.

As discussed in U.S. Pat. No. 5,383,858, a syringe used with a front-loading injector requires a specially designed readily releasable mounting mechanism for securing the syringe to the front wall of the injector head and a specially designed readily releasable mounting mechanism for securing the syringe plunger to the piston head of the injector. These required mounting mechanisms oftentimes increase the cost of the syringes and prohibit the use of syringes of other various types with front-loading injectors. Syringes of other various types generally include a syringe body, a plunger reciprocally mounted therein, and a plunger extension engagable by a drive means. Thus, it is desirable to design an adapter for use with syringes of various types to permit use of these syringes with front-loading injectors.

SUMMARY OF THE INVENTION

The present invention relates to adapters for releasably attaching syringes of various types to front-loading injectors. As more fully described in U.S. Pat. No. 5,383,858, front-loading injectors have an injector head, including a front wall and an opening formed therein, and a drive member, such as a piston having a piston head, reciprocally mounted within the injector head and extendible through the injector head opening.

By way of example, a syringe of a first type includes a body, a plunger reciprocally mounted therein, and a plunger rod attached to the rear end of the plunger and extending axially out of the syringe body. A circumferential flange is disposed about the rear end of the syringe body and a circumferential flange is disposed about the rear end of the plunger rod.

The syringe adapter of the first embodiment of the invention permits use of a syringe of the first type with a front-loading injector and includes a carrier having a rear end, a front end, and an arcuate channel formed near the front end of the carrier to engage at least a portion of the circumferential flange located at the rear end of the syringe. A pair of mounting flanges is located proximate to the carder rear end for releasably mounting the carrier in a desired position relative to the front wall of the injector head. The pair of mounting flanges and corresponding pair of receiving flanges of the injector head form a first interlocking mechanism which is activated and released upon rotation of the carrier relative to the front wall of the injector head. The mounting flanges may also include indicating means, such as recesses or notches, which may be read by the injector, by any suitable means, so as to identify the type of syringe and/or adapter installed onto the injector head.

The syringe adapter of the first embodiment further includes a follower reciprocally mounted within the carrier. The follower includes a rear end, and a front end having an arcuate channel formed therein for receiving a least: a portion of the circumferential flange disposed about the rear end of the syringe plunger rod. A piston head opening and a pair of piston head slots communicating therewith are formed in the rear end of the follower. The piston head opening and piston head slots form a second interlocking mechanism with the piston head which is activated and released upon rotation of the carrier relative to the front wall of the injector head.

By way of another example, a syringe of a second type includes a body, a neck portion, a tapered section connecting the body and neck portion, a plunger reciprocally mounted within the body, and a flange circumferentially disposed near the rear end of the body. The syringe of the second type further includes a plunger extension extending from the rear of the plunger, which includes a knob connected to a stem portion. When a syringe of the second type is installed into an injector other than a front-loading injector, the knob typically engages the drive means of such injector.

The adapter of the second embodiment permits use of the second type of syringe with a front-loading injector and includes a carrier having a front end, a rear end and an arcuate channel formed near the rear end of the carrier to engage at least a portion of the circumferential flange located at the rear end of the syringe. A front retaining wall is further provided proximate to the carrier front end for engaging at least a portion of a front tapered section of the syringe when the syringe is installed in the carrier. Similar to the first embodiment of the invention, a pair of mounting flanges is located proximate to the carrier rear end for releasably mounting the carrier in a desired position relative to the front wall of the injector head. The pair of mounting flanges and corresponding pair of receiving flanges of the injector head form a first interlocking mechanism which is activated and released upon rotation of the carrier :relative to the front wall of the injector head.

The syringe adapter of the second embodiment further includes a follower reciprocally mounted within the carrier. The follower includes a rear end, and a front end having a radial channel formed therein for receiving the knob and stem of the plunger extension. Similar to the first embodiment, a piston head opening and a pair of piston slots communicating therewith are formed in the rear end of the follower. The piston head opening and piston slots form a second interlocking mechanism with the piston head which is activated and released upon rotation of the carrier relative to the front wall of the injector head.

The syringe adapter of the third embodiment of the invention is an alternative to the second embodiment and permits use of a syringe, of the second type with a front-loading injector. This adapter embodiment includes a carrier having a front end, a rear end and an arcuate channel formed in the carrier to engage at least a portion of the circumferential flange located at the rear end of the syringe. In this embodiment, the syringe body, when installed in the carrier, extends beyond the front end of the carrier. Similar to the second embodiment of the invention, this embodiment includes a pair of mounting flanges located proximate to the carrier rear end for mounting the carrier in a desired position relative to the front wall of the injector head. These mounting flanges operate as described above. Further, this embodiment includes a follower having the elements and function similar to the follower of the second embodiment, as described above.

DETAILED DESCRIPTION OF THE INVENTION

Figure 1A:
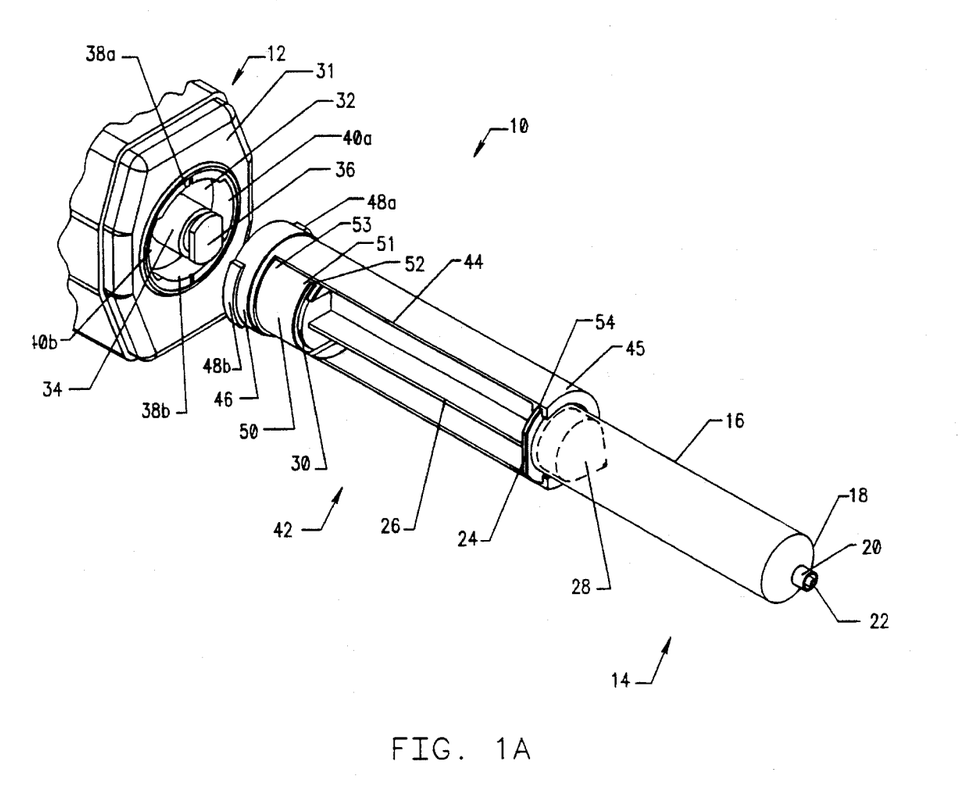
FIG. 1A is a perspective, disassembled view of an injector of a front-loading type and a first embodiment of a syringe/adapter combination the present invention.

FIG. 1A shows a disassembled view of a front-loading medical injection system 10 comprising and injector (not shown) having a front-loading injector head 12 onto which a syringe 14 of any type is attached. By way of example, syringe 14 includes a syringe body 16 and a neck portion 20 connected thereto by a tapered portion 18. A standard luer connector 22 may also be provided for attaching a fluid delivery path (not shown) to a patient. Body 16 may also include a flange 24 circumferentially disposed near its rear end. A plunger 28 is reciprocally mounted within the syringe body 16 any may include a plunger extension, such as plunger rod 26 having a flange 30 circumferentially disposed near the rear end of the plunger rod 26.

The front-loading injector head 12 includes a front wall 31 having an opening 32 formed therein. A drive means, such as piston 34, is reciprocally mounted within head 12 and is extendible through opening 32. Piston 34 includes a piston head 36. Receiving flanges 38a and 38b, preferably positioned opposite one another, radially extend inwardly into opening 32. Receiving slots 40a and 40b, preferably positioned opposite one another and between receiving flanges 38a and 38b, respectively, also radially extend inwardly into opening 32. The function of receiving flanges 38a and 38b, and receiving slots 40a and 40b, is described below.

The first embodiment of the syringe adapter 42 of the present invention, as shown in FIGS. 1A through 2E, includes a carrier 44 having a front end 45 and a rear end 46. Means for retaining the syringe, such as circumferential slot 54 or any other suitable mechanism, is provided at the front end 45 of carrier 42 to receive and retain syringe flange 24 within the carrier 42 during an injection procedure. As best shown in FIGS. 2A–2E the rear end 46 of carrier 42 includes a first readily releasable mounting means, such as a pair of mounting flanges 48a and 48b, for mounting the carrier 42 in a desired position relative to the front wall 31 of the injector head 12. Mounting flanges 48a and 48b may include indicating means, such as detents or notches 57a and 57b, which provide information to the injector head 12 about the type of syringe 14 or adapter 42 being used. Correspondingly, the injector head 12 includes any suitable means (not shown) for reading information from notches 57a and 57b.

Figure 2A:
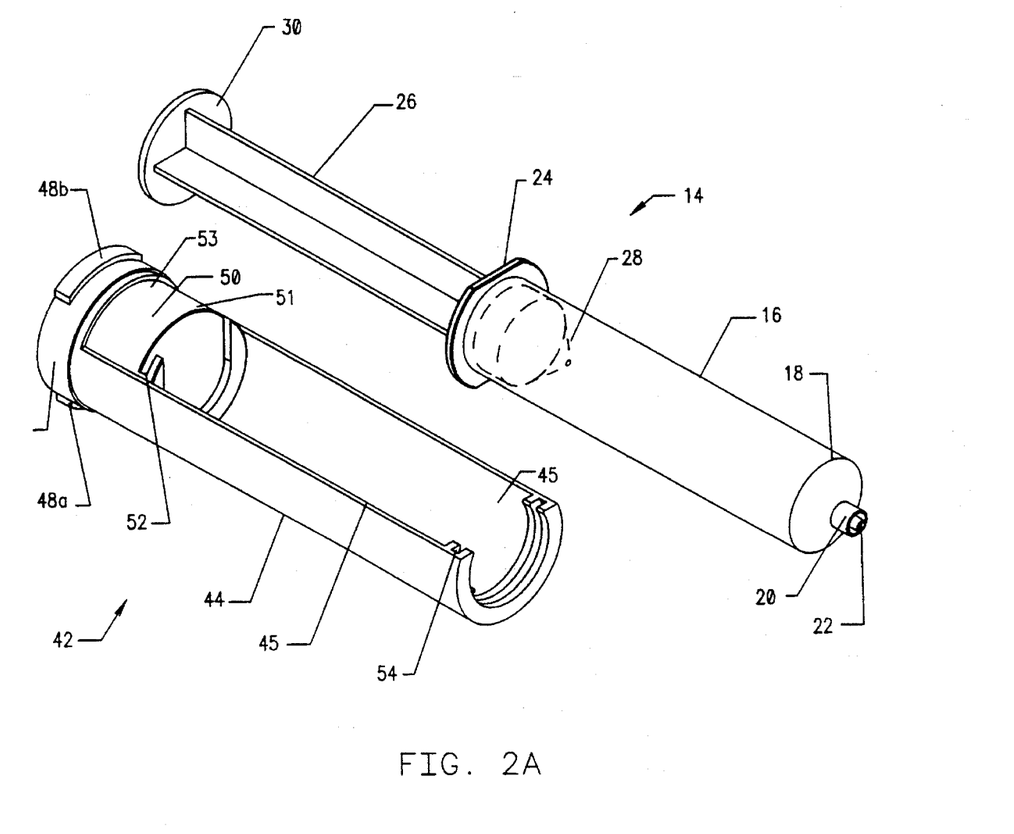
FIG. 2A is a perspective, disassembled view of a syringe and the first embodiment of the syringe adapter of the present invention.
Figure 2B:
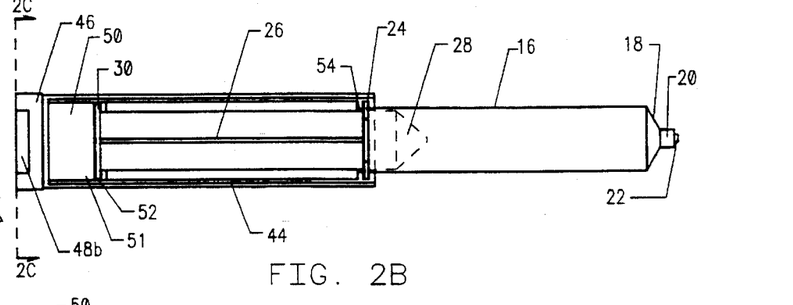
FIG. 2B is a top view of the first embodiment of an assembled syringe/adapter combination shown in FIG. 2A.
Figure 2C:
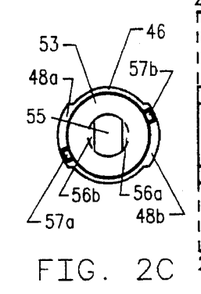
FIG. 2C is an end view of the first embodiment of the syringe/adapter combination taken along line 2C—2C of FIG. 2B.
Figure 2D:
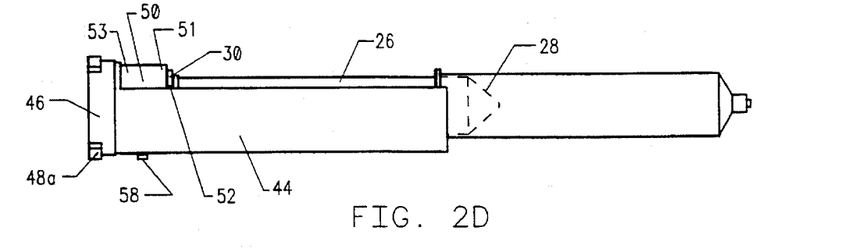
FIG. 2D is a side view of the first embodiment of the syringe/adapter combination shown in FIG. 2B.
Figure 2E:
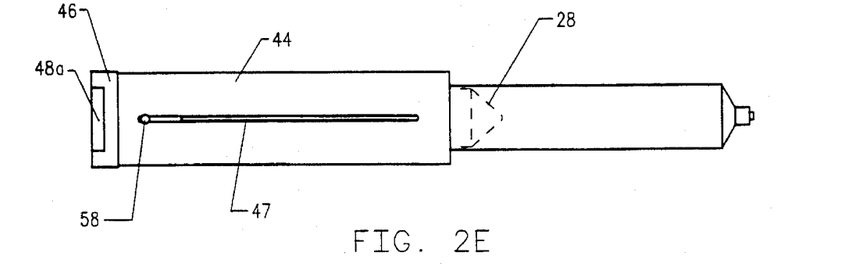
FIG. 2E is a bottom view of the first embodiment of the syringe/adapter combination shown in FIG. 2B.

The adapter of the first embodiment further includes a follower 50 reciprocally mounted within the carrier 44 and includes a front end 51 and a rear end 53. The front end 51 includes a circumferential slot 52 which receives and retains flange 30 of plunger rod 26 when syringe 14 is installed into adapter 42. As best shown in FIG. 2C, the rear end 53 of follower 50 includes second readily releasable mounting means, such as piston head opening 55, and piston slots 56a and 56b recessed behind and communicating therewith, for mounting the follower 50 in a desired position relative to the piston head 36. It is understood that rear end 53 of follower 50 may include various other mechanisms for releasably mounting the follower to the piston head, such as L-shaped members, as taught in U.S. Pat. No. 5,383,858, or any type of clip device. As shown in FIGS. 2D and 2E, carrier 44 may further include an axial slot 47 for receiving follower alignment peg 58 extending from the bottom of follower 50. As follower alignment peg 58 moves axially within slot 47, it ensures that follower 50 will not rotate within carrier 44 during an injection procedure.

To use the adapter 42 to attach syringe 14 to injector head 12, it is preferred that the operator first insert syringe 14 into adapter 42 such that syringe body flange 24 is received by carrier slot 54 and plunger rod flange 30 is received by follower slot 52. Rear end of adapter 46 is then inserted into injector head opening 32 such that mounting flanges 48a and 48b are inserted into receiving slots 40a and 40b, respectively. If, at this time, follower 50 is not positioned at the rear end 46 of carrier 42 such that piston head opening 55 can engage piston head 36, the piston 34 is moved forward by the operation of the injector to advance the piston head 36 until the piston head 36 is received by the piston head opening 55 of follower 50.

Once mounting flanges 48a and 48b are inserted into receiving slots 40a and 40b, respectively, and the piston head 36 is received by the piston head opening 55, the operator rotates the entire adapter/syringe combination approximately 90 degrees such that mounting flanges 48a and 48b move behind and are engaged by receiving flanges 38a and 38b, respectively, and the piston head 36 moves into piston slots 56a and 56b. Injector head 12 may further include a stop mechanism (not shown) extending from at least one of the retaining slots 38a and 38b, to prevent rotation of the adapter/syringe combination more than 90 degrees. The adapter/syringe combination is now securely attached to injector head 12 and the operator can begin the injection procedure. As piston 34 is advanced forward, follower 50 applies a motive force to plunger rod 26 which advances plunger 28, thus, forcing fluid in syringe 14 out of neck 20 into the fluid path (not shown) to the patient.

Once the injection procedure is completed, the operator grasps the adapter/syringe combination and rotates it 90 degrees back to the pre-installation orientation, thus, disengaging the mounting flanges 48a and 48b from behind receiving flanges 38a and 38b, respectively, and disengaging piston head 36 from piston slots 56a and 56b. The adapter/syringe combination is then removed from the injector head 12.

A primary advantage of using adapter 42 is that syringe 14 need not include mounting flanges and its plunger 28 need not include means for receiving the piston head, as required by the from-loading syringes taught in U.S. Pat. No. 5,383,858. Thus, the cost of syringe 14 is reduced. Other advantages of using adapter 42 are that syringe 14 can be loaded onto and removed from injector head 12 without disassembling the fluid path to the patient, and the injector piston 34 may be retracted from adapter/syringe combination without retracting syringe plunger 28, thus, reducing the risk of withdrawing fluid from the patient back into the syringe 14.

Figure 3A:
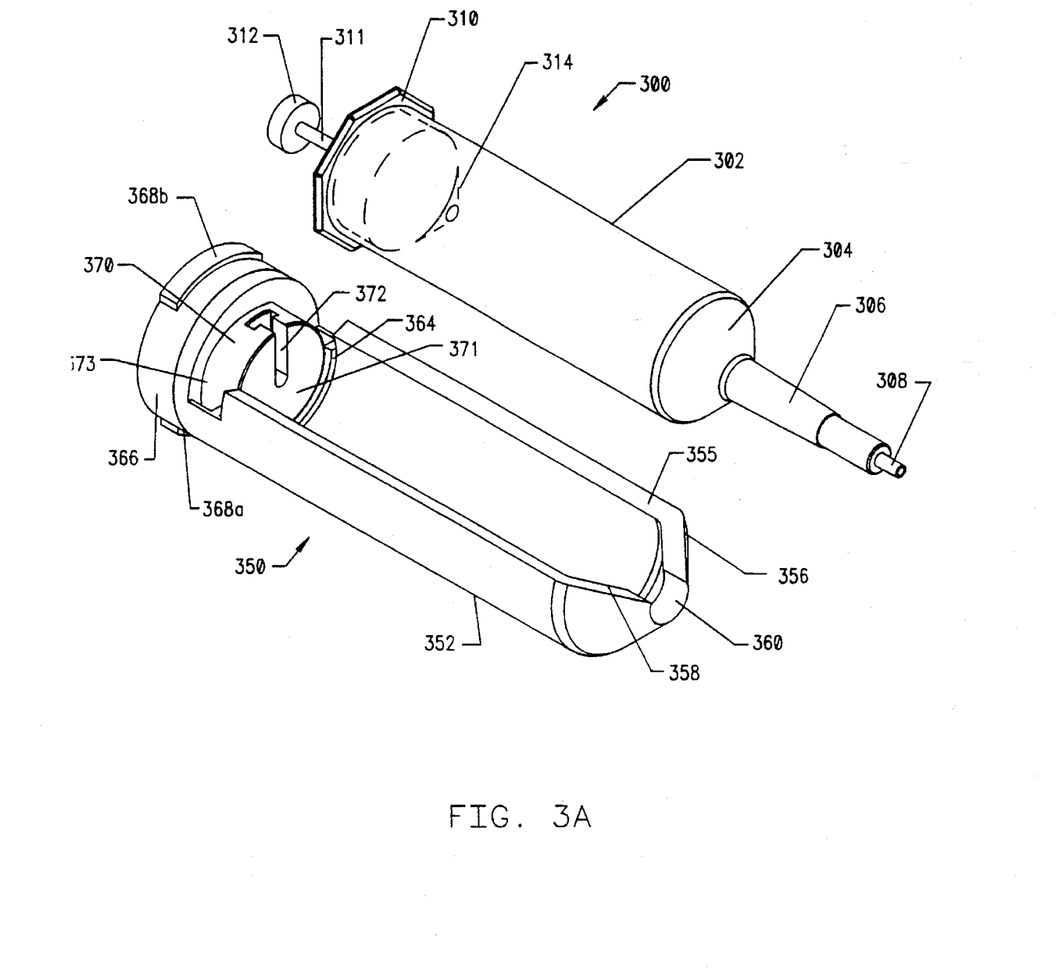
FIG. 3A is a perspective, disassembled view of a syringe and a second embodiment of the syringe adapter of the present invention.
Figure 3B:
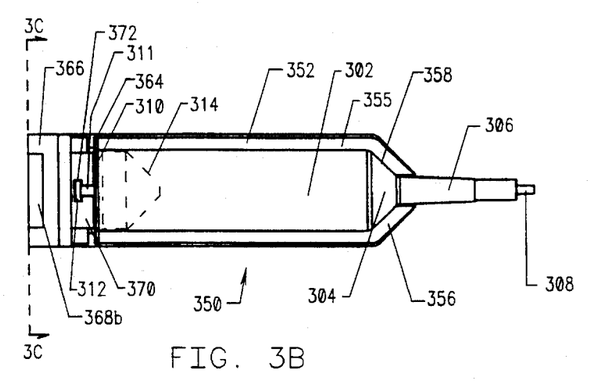
FIG. 3B is a top view of the second embodiment of an assembled syringe/adapter shown in FIG. 3A.

It is understood that syringes of other configurations may be used with the adapters of the present invention. For example, as shown in FIG. 3 A, a syringe 300 of a second type may include a syringe body 302 and a neck portion 306 connected thereto by a tapered portion 304. A standard luer connector 308 may also be provided for attaching a fluid delivery path (not shown) to a patient. Body 302 may further include a flange 310 circumferentially disposed near its rear end. A plunger 314 is reciprocally mounted within the syringe body 302 and may include a plunger extension, such as plunger stem 311 having a knob 312 attached thereto. When a syringe of this type is used with an injector other than the front-loading injector described herein, knob 312 is typically engaged by the injector drive means. The front-loading injector head onto which syringe 300 is releasably attached is similar to the front-loading injector head 12 shown in FIGS. 1A and 1B, and previously described.

The second embodiment of the syringe adapter 350 of the present invention, as shown in FIGS. 3A through 3D, includes a carrier 352 having a from end 355 and a rear end 366. Means for retaining the syringe, such as circumferential slot 364 or any other suitable mechanism, is provided proximate to the rear end 366 of carrier 350 to receive and retain syringe flange 310 within the carrier 350 during an injection procedure. A front retaining wall 356 is provided at the front end 355 of carrier 350 and includes an inside surface 358 which engages and retains at least a portion of the syringe tapered section 304, and opening 360 which engages and retains at least a portion of the syringe neck 306, when syringe 300 is installed into carrier 350.

Similar to the first embodiment of the invention, the rear end 366 of carrier 350 includes a first readily releasably mounting means, such as a pair of mounting flanges 368a and 368b, for mounting the carrier 350 in a desired position relative to the front wall 31 of the injector head 12. Mounting flanges 368a and 368b may include indicating means, such as detents or notches 369a and 369b, which provide information to the injector head 12 about the type of syringe 300 or adapter 350 being used.

Figure 3C:
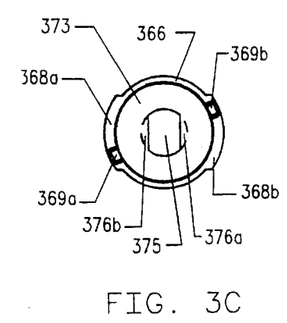
FIG. 3C is an end view of the second embodiment of the syringe/adapter combination taken along line 3C—3C of FIG. 3B.
Figure 3D:
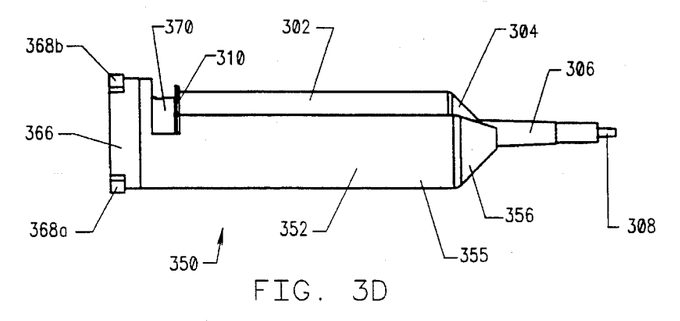
FIG. 3D is a side view of the second embodiment of the syringe/adapter combination shown in FIG. 3B.

The adapter of the second embodiment further includes a follower 370 reciprocally mounted within the carrier 350 and includes a front end 371 and a rear end 373. The front end 371 includes a slot 372 configured to receive the stem 311 and knob 312 of plunger 314 when syringe 300 is installed into adapter 350. FIG. 3C, shows that rear end 373 of follower 370 includes second readily releasable mounting means, such as piston head opening 375, and piston slots 376a and 376b recessed behind piston opening 375 and communicating therewith, for mounting the follower 370 in a desired position relative to the injector piston head 36.

Use of adapter 350 is similar to use of the adapter of the first embodiment. To attach syringe 300 to injector head 12 of FIGS. 1A and 1B, the operator first inserts syringe 300 into adapter 350 such that syringe body flange 310 is received by carrier slot 364, and plunger stem 311 and knob 312 are received by follower slot 372 such that the front end 371 of follower 370 engages the rear surface of plunger 314. Rear end 366 of adapter 350 is then inserted into injector head opening 32 such that mounting flanges 368a and 368b are inserted into injector head receiving slots 40a and 40b, respectively. If, at this time, follower 370 is not positioned at the rear end 366 of carrier 350 such that piston head opening 375 can engage piston head 36, the piston 34 is moved forward by the operation of the injector to advance the piston head 36 until the piston head 36 is received by the piston head opening 375 of follower 370.

Once mounting flanges 368a and 368b are inserted into injector receiving slots 40a and 40b, respectively, and the piston head 36 is received by the piston head opening 375, the operator rotates the entire adapter/syringe combination approximately 90 degrees such that mounting flanges 368a and 368b move behind and are engaged by receiving flanges 38a and 38b, respectively, and the piston head 36 moves into piston slots 376a and 376b. The adapter/syringe combination is now securely attached to injector head 12 and the operator can begin the injection procedure. As piston 34 is advanced forward, follower 370 applies a motive force to the rear face of plunger 314, thus, forcing fluid in syringe 300 out of neck 306 into the fluid path (not shown) to the patient.

Once the injection procedure is completed, the operator grasps the adapter/syringe combination and rotates it 90 degrees back to the pre-installation orientation, thus, disengaging the mounting flanges 368a and 368b from behind injector receiving flanges 38a and 38b, respectively, and disengaging piston head 36 from piston slots 376a and 376b. The adapter/syringe combination is then removed from the injector head 12.

The advantages of using the adapter of the first embodiment of the invention are also achieved by using the adapter of the second embodiment of the invention.

Figure 1B:
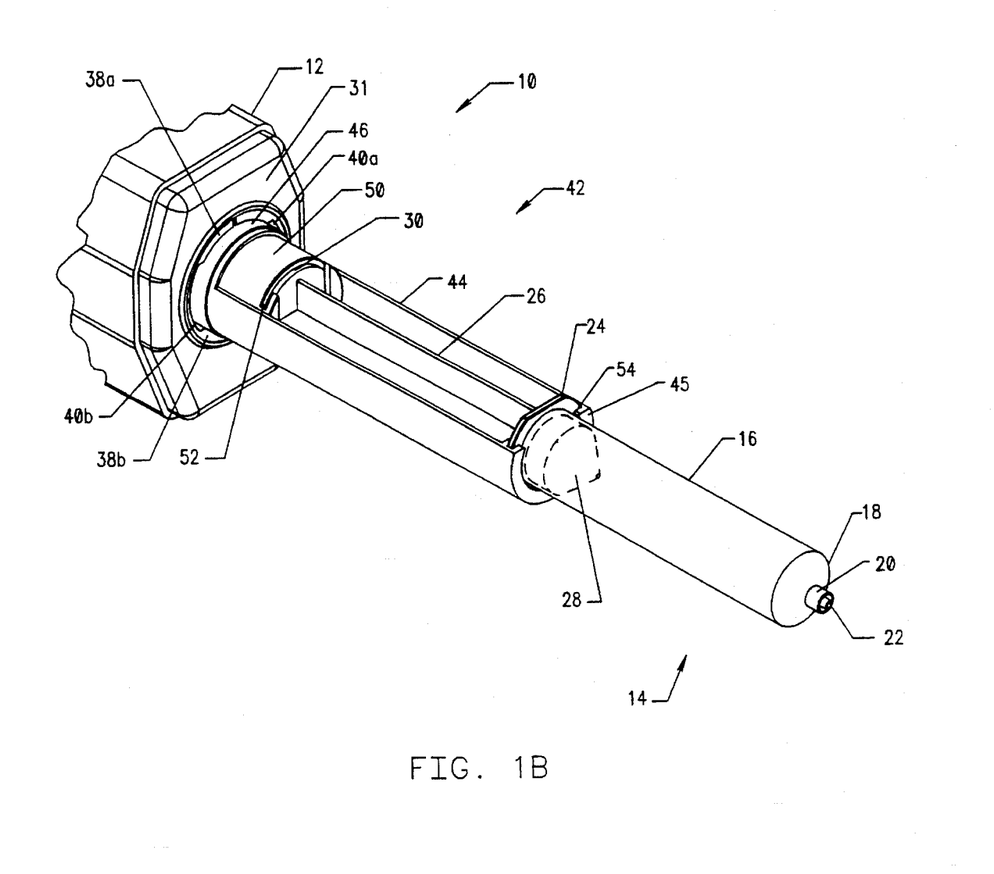
FIG. 1B is a perspective view of the syringe/adapter combination of FIG. 1A loaded onto the front-loading injector of FIG. 1A.
Figure 4A:
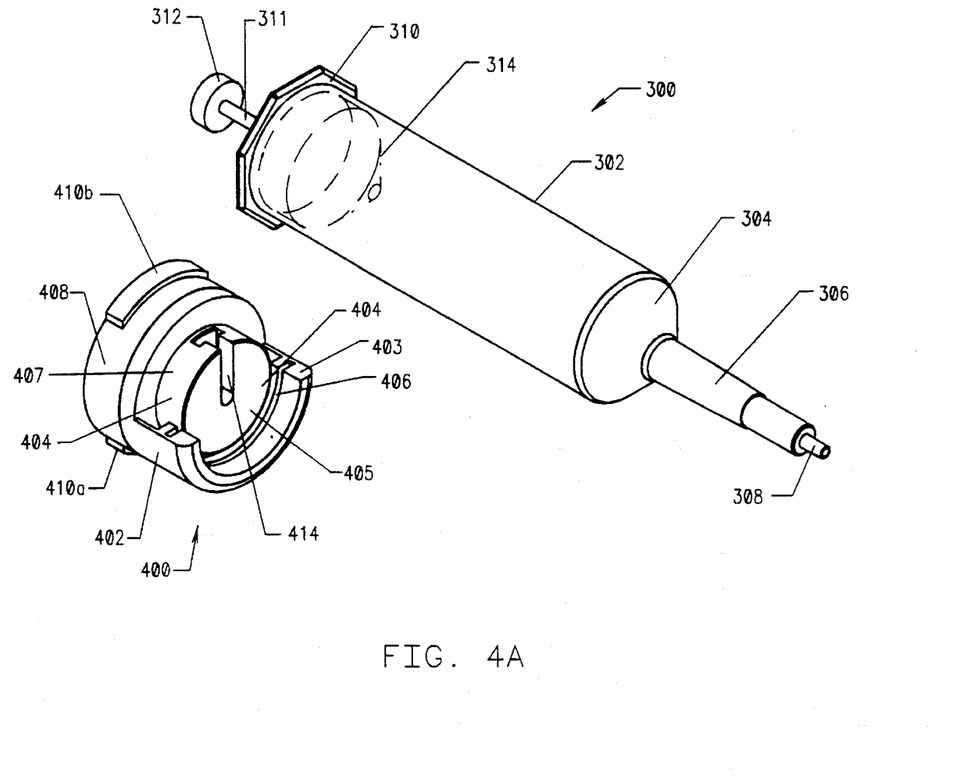
FIG. 4A is a perspective, disassembled view of a syringe and a third embodiment of the syringe adapter of the present invention.
Figure 4B:
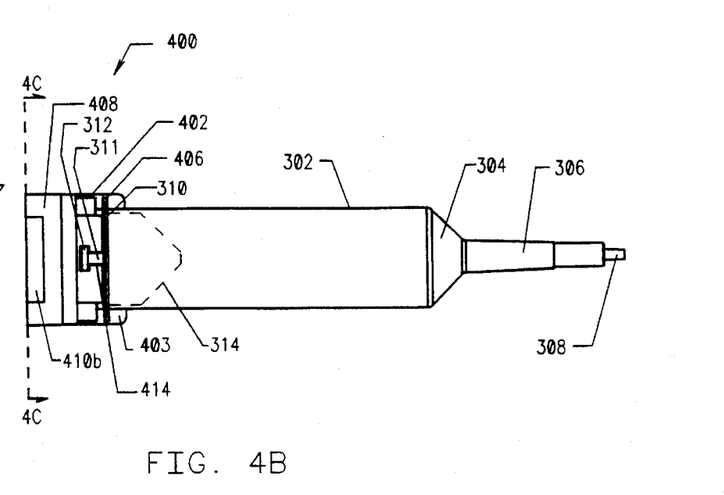
FIG. 4B is a top view of the third embodiment of an assembled syringe/adapter combination shown in FIG. 4A.

The third embodiment of syringe adapter of the present invention is similar to the second embodiment in that it permits use of a syringe of the second type, as shown in FIG. 3A, and reproduced in FIG. 4A, with a the front-loading injector shown in FIGS. 1A and 1B. As shown in FIGS. 4A through 4D, the adapter 400 of the third embodiment includes a carrier 402 having a front end 403 and a rear end 408. Means for retaining the syringe, such as a circumferential slot 406 or any other suitable mechanism, is formed within carrier 400 to receive and retain syringe flange 310 within the carrier 400 during an injection procedure. Unlike the second embodiment, the third embodiment of the adapter does not include the front retaining wall, as previously described.

Figure 4C:
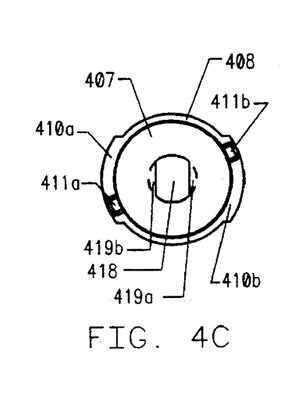
FIG. 4C is an end view of the third embodiment of the syringe/adapter combination taken along line 4C—4C of FIG. 4B.
Figure 4D:
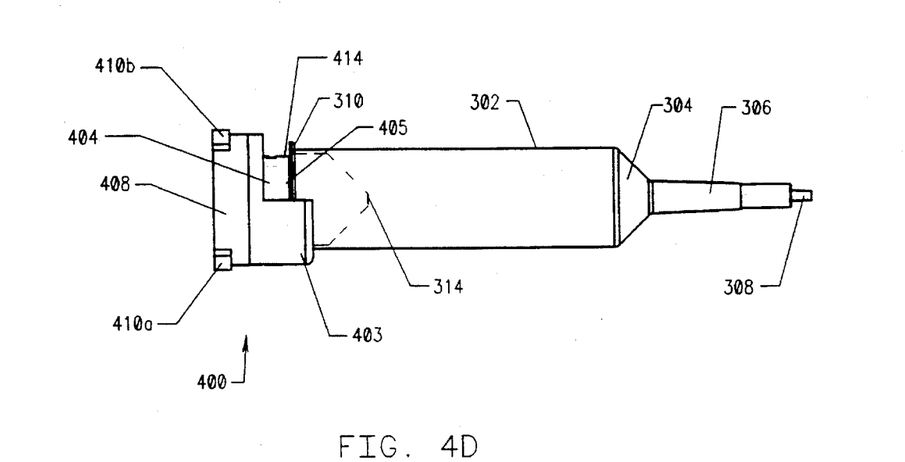
FIG. 4D is a side view of the third embodiment of the syringe/adapter combination shown in FIG. 4B.

Similar to the first and second embodiments, the rear end 408 of carrier 400 of the third embodiment includes a first readily releasably mounting means, such as a pair of mounting flanges 410a and 410b, for mounting the carrier 400 in a desired position relative to the front wall 31 of the injector head 12. Mounting flanges 410a and 410b may further include indicating means, such as detents or notches 411a and 411b, which provide syringe and/or adapter information to the injector head 12. Similar to the second embodiment, the adapter 400 of the third embodiment further includes a follower 404 reciprocally mounted within the carrier 400 which includes a front end 405 and a rear end 407. As shown in FIG. 4A, the front end 405 includes a slot 414 configured to receive the stem 311 and knob 312 of plunger 314 when syringe 300 is installed into adapter 350. FIG. 4C, shows that rear end 407 of follower 404 includes second readily releasable mounting means, such as piston head opening 418, and piston slots 419a and 419b recessed behind piston opening 418 and communicating therewith, for mounting the follower 404 in a desired position relative to the piston head 36.

Use of adapter 400 is similar to use of the adapters of the first and second embodiments. To attach syringe 300 to injector head 12 of FIGS. 1A and 1B, the operator first inserts syringe 300 into adapter 400 such that syringe body flange 310 is received by carrier slot 406, and plunger stem 311 and knob 312 are received by follower slot 414 such that the front end 405 of follower 404 engages the rear surface of plunger 314. Rear end 408 of adapter 400 is then inserted into injector head opening 32 such that mounting flanges 410a and 410b are inserted into injector head receiving slots 40a and 40b, respectively. If, at this time, follower 404 is not positioned at the rear end 408 of carrier 400 such that piston head opening 418 can engage piston head 36, the piston 34 is moved forward by the operation of the injector to advance the piston head 36 until the piston head 36 is received by the piston head opening 418 of follower 404.

Once mounting flanges 410a and 410b are inserted into injector receiving slots 40a and 40b, respectively, and the piston head 36 is received by the piston head opening 418, the operator rotates the entire adapter/syringe combination approximately 90 degrees such that mounting flanges 410a and 410b move behind and are engaged by receiving flanges 38a and 38b, respectively, and the piston head 36 moves into piston slots 419a and 419b. The adapter/syringe combination is now securely attached to injector head 12 and the operator can begin the injection procedure. As piston 34 is advanced forward, follower 404 applies a motive force to the rear face of plunger 314, thus, forcing fluid in syringe 300 out of neck 306 into the fluid path (not shown) to the patient.

Once the injection procedure is completed, the operator grasps the adapter/syringe combination and rotates it 90 degrees back to the pre-installation orientation, thus, disengaging the mounting flanges 410a and 410b from behind injector receiving flanges 38a and 38b, respectively, and disengaging piston head 36 from piston slots 419a and 419b. The adapter/syringe combination is then removed from the injector head 12.

The advantages of using the adapter of the first embodiment of the invention are also achieved by using the adapter of the third embodiment of the invention.

Although the syringe adapters of the invention have been described in detail for the purpose of illustration, it is to be understood that such detail is solely for that purpose and that variations can be made thereto by those skilled in the art without departing from the spirit and scope of the invention except as it may be limited by the claims

We claim:

1. An adapter for releasably attaching a syringe to a front-loading injector head, wherein the syringe includes a body, and a plunger reciprocally mounted therein, and wherein the injector head includes a front wall, an opening formed therein, and a drive member having a drive head reciprocally mounted within the injector head and extendible through the opening, the adapter comprising:

a syringe carrier having a front end, a rear end, and syringe retaining means located between the carrier front end and rear end for engaging at least a portion of the syringe to retain the syringe within at least a portion of the carrier during an injection procedure;

first readily releasable mounting means positioned proximate to the carrier rear end for mounting the carrier in a desired position relative to the front wall of the injector head;

a follower reciprocally mounted within the carrier and including a front end and a rear end, the front end engagable with the syringe plunger when the syringe is installed in the carrier; and second readily releasable mounting means positioned proximate to the rear end of the follower for mounting the follower in a desired position relative to the drive head.

2. The adapter of claim 1 wherein the syringe retaining means is positioned proximate to the carrier front end.

3. The adapter of claim 1 wherein the syringe retaining means is positioned proximate to the carrier rear end.

4. The adapter of claim 1 wherein the syringe retaining means includes a channel for receiving at least a portion of a flange disposed proximate to a rear end of the syringe body.

5. The adapter of claim 1 wherein the carrier further comprises:

a front retaining wall positioned proximate to the carrier front end for engaging at least a portion of a front tapered section of the syringe.

6. The adapter of claim 1 wherein the first readily releasable mounting means is engagable with a first readily releasable receiving means positioned proximate the injector head opening to form a first interlocking mechanism which is activated and released upon rotation of the carrier relative to the front wall of the injector head.

7. The adapter of claim 1 wherein the first readily releasable mounting means includes at least one mounting flange extending radially outward proximate to the rear end of the carrier, the mounting flange releasably engagable with at least one receiving flange extending radially inward proximate to the opening in the front wall of the injector head upon rotation of the carrier relative to the front wall of the injector head.

8. The adapter of claim 7 wherein the mounting flange includes indication means for providing information identifying at least one of the syringe and adapter loaded onto the injector head.

9. The adapter of claim 1 wherein the follower includes means for releasably receiving at least a portion of a plunger extension extending from a rear end of the plunger.

10. The adapter of claim 9 wherein the plunger extension includes a plunger rod attached at a first end to the plunger and having a flange disposed proximate to a second end of the plunger rod; and the means for releasably receiving at least a portion of the plunger extension includes means for releasably receiving at least a portion of the plunger rod flange.

11. The adapter of claim 10 wherein the means for releasably receiving at least a portion of the plunger rod flange includes a channel formed proximate to the front end of the follower.

12. The adapter of claim 9 wherein the plunger extension includes a stem attached at a first end to the plunger and knob attached to a second end of the stem; and the means for releasably receiving at least a portion of the plunger extension includes means for releasably receiving at least a portion of the stem and knob.

13. The adapter of claim 12 wherein the means for releasably receiving at least a portion of the stem and knob includes a channel formed proximate to the front end of the follower, the channel radially extending from an edge of the follower to a center of the follower.

14. The adapter of claim 1 wherein the second readily releasable mounting means is engagable with the injector drive head to form a second interlocking mechanism which is activated and released upon rotation of the carrier relative to the front wall of the injector head.

15. The adapter of claim 1 wherein the second readily releasable mounting means includes a drive head opening and a pair of drive head slots communicating therewith, the drive head opening and drive head slots releasably engagable with the drive head upon rotation of the carrier relative to the front wall of the injector head.

16. A syringe system for use with a front-loading injector head wherein the injector head includes a front wall and an opening formed therein, and a drive member having a drive head reciprocally mounted within the injector head and extendible through the opening, the system comprising:

a syringe including a body, and a plunger reciprocally mounted therein; and an adapter for receiving the syringe and including a carrier having a front end, a rear end, and syringe retaining means located between the carrier front and rear ends for engaging at least a portion of the syringe to retain the syringe within the carrier during an injection procedure;

first readily releasable mounting means positioned proximate to the carrier rear end for mounting the carrier in a desired position relative to the front wall of the injector housing;

a follower reciprocally mounted within the carrier and including a front end and a rear end, the front end engagable with the syringe plunger when the syringe is installed in the carrier; and second readily releasable mounting means positioned proximate to the rear end of the follower for mounting the follower in a desired position relative to the drive head.

17. The syringe system of claim 16 wherein the first readily releasable mounting means is engagable with a first readily releasable receiving means positioned proximate the injector head opening to form a first interlocking mechanism which is activated and released upon rotation of the carrier relative to the front wall of the injector head.

18. The syringe system of claim 16 wherein the follower includes means for releasably receiving at least a portion of a plunger extension extending from a rear end of the plunger.

19. The syringe system of claim 18 wherein the means for releasably receiving at least a portion of the plunger extension includes a channel formed proximate to the front end of the follower.

20. The syringe system of claim 16 wherein the second readily releasable mounting means is engagable with the injector drive head to form a second interlocking mechanism which is activated and released upon rotation of the carrier relative to the front wall of the injector head.

* * * * *